United States Patent
Lyons (10) Patent No.: US 8,034,045 B1
(45) Date of Patent: Oct. 11, 2011

(54) FLEXIBLE SHEATH

(75) Inventor: Drew P. Lyons, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/774,269

(22) Filed: May 5, 2010

(51) Int. Cl.
*A61M 25/00* (2006.01)

(52) U.S. Cl. ........ 604/526; 604/523; 604/524; 604/525; 604/527

(58) Field of Classification Search .............. 604/158, 604/523–527
See application file for complete search history.

(56) References Cited

U.S. PATENT DOCUMENTS

| | | | |
|---|---|---|---|
| 419,926 A | 1/1890 | Chapman | |
| 4,172,474 A | 10/1979 | Stahl | 138/132 |
| 5,069,674 A | 12/1991 | Fearnot et al. | 604/282 |
| 5,405,338 A | 4/1995 | Kranys | 604/282 |
| 5,423,774 A | 6/1995 | Fischell et al. | 604/282 |
| 5,755,704 A | 5/1998 | Lunn | 604/282 |
| 5,827,201 A | 10/1998 | Samson et al. | 600/585 |
| 5,873,866 A | 2/1999 | Kondo et al. | 604/280 |
| 5,997,487 A | 12/1999 | Kolehmainen et al. | 600/585 |
| 6,033,394 A | 3/2000 | Vidlund et al. | 604/524 |
| 6,036,670 A | 3/2000 | Wijeratne et al. | 604/96 |
| 6,053,903 A * | 4/2000 | Samson | 604/526 |
| 6,939,337 B2 | 9/2005 | Parker et al. | 604/528 |
| 2008/0051694 A1 | 2/2008 | Kato | 604/22 |
| 2010/0057051 A1* | 3/2010 | Howat et al. | 604/526 |

FOREIGN PATENT DOCUMENTS

| | | |
|---|---|---|
| EP | 1 123 714 A1 | 8/2001 |
| EP | 1 955 724 A1 | 8/2008 |
| WO | WO 2006/060312 A1 | 6/2006 |

OTHER PUBLICATIONS

International Search Report and Written Opinion issued in PCT/US2011/033196 dated Aug. 2, 2011, 14 pgs.

* cited by examiner

*Primary Examiner* — Theodore Stigell
*Assistant Examiner* — Bradley Thomas, Jr.
(74) *Attorney, Agent, or Firm* — Brinks Hofer Gilson & Lione (57) ABSTRACT

A medical device including a sheath having an inner liner and an outer layer attachable to a coil independent from each other to allow the inner liner and the outer layer the freedom to move coaxially independent from each other. The coil can be closely wound at a predetermined coil spacing sufficient to inhibit portions of the outer layer from entering into voids between the adjacent coil windings. Intermediate layers for bonding between the coil and the inner liner and/or the outer layer may also be provided. A filler material can be disposed within the voids between the adjacent windings of the coil. The filler material has a dimension sized to bridge the void between adjacent coil windings in order to inhibit portions of the outer layer from bonding to the inner liner. The filler material can be in the form of a ribbon.

19 Claims, 8 Drawing Sheets

FLEXIBLE SHEATH

TECHNICAL FIELD

This invention relates generally to a medical device, and more particularly, to a tubular device for enhancing access to the vascular system of a patient.

BACKGROUND

Among the most important advances in modern medical practice has been the adoption of a variety of minimally invasive procedures. Examples of such minimally invasive procedures include angioplasty, endoscopy, laparoscopy, arthroscopy and the like. Minimally invasive surgical procedures such as these can be distinguished from conventional open surgical procedures. In these minimally invasive procedures, access to a target site within the body of a patient is achieved through a relatively small incision, into which a tubular device (including a tube of a device) is inserted or introduced. The tubular device maintains the patency of the incision, while permitting access to the target site via the interior (lumen) of the device.

In order to reach the target site, the tubular devices are often required to traverse tortuous pathways having sharp bends and angles. In some instances, and particularly when traversing such tortuous pathways, the tubular devices exhibit a tendency to kink. Kinking reduces, and often collapses, the effective inner diameter of the tubular device, thereby typically rendering the tubular device unsuitable for its intended use. Once a tubular device kinks, fluid cannot pass through the lumen of its shaft, and it becomes essentially useless, e.g., preventing inflation of balloon catheters and fluid delivery in diagnostic, infusion and drainage catheters for their satisfactory use. As a result, the initially introduced tubular device must be removed, and another tubular device must then be introduced into the patient and once again advanced through the vascular system to the narrowed site. This wastes time and increases the potential for trauma to the patient.

The tendency of a tubular device to kink is increased when the tubular device is used to introduce an interventional device into one of the many smaller vessels that branch off from major vessels. In this event, the tubular device may have insufficient flexibility at the very point where flexibility is most desired in order to enable proper positioning of the interventional device. In order to traverse the narrow confines of, e.g., the vascular system, the tubular device is typically formed of thin-wall construction. However, thin walled tubular devices often have difficulty tracking narrow vessels, and exhibit an increased propensity to kink. Increasing the thickness of the sheath tube can minimally improve the level of kink resistance, as well as the trackability of the tubular device, but limits the ability of the sheath to enter a narrow vessel, and reduces the diameter of the lumen when compared to the lumen of an otherwise similar thin-walled sheath.

To inhibit kinking, some tubular devices include a coil embedded in the wall of the catheter shaft, while other tubular devices include both a coil and a braid to take advantage of these features. One such device is found in U.S. Pat. No. 6,939,337, assigned to the assignee herein, which discloses a tubular medical device that includes a coil, such as a flat wire coil, in a stressed radially expanded condition, and a braid that extends over at least part of the coil. A bonding layer, formed from a polymer such as nylon or polyurethane, is positioned over and contacts the coil, or both the coil and the braid. The polymeric bonding layer maintains the coil in the stressed radially expanded condition, and is bonded to an inner liner, such as PTFE. By providing both a coil and a braid, the tubular device achieves some advantages attainable from each of these reinforcements. For example, the coil enables the device to better resist collapse, necking and kinking during use. The braid provides the device with enhanced pushability, trackability and torqueability. The '337 patent is incorporated by reference herein in its entirety.

Figure 1:
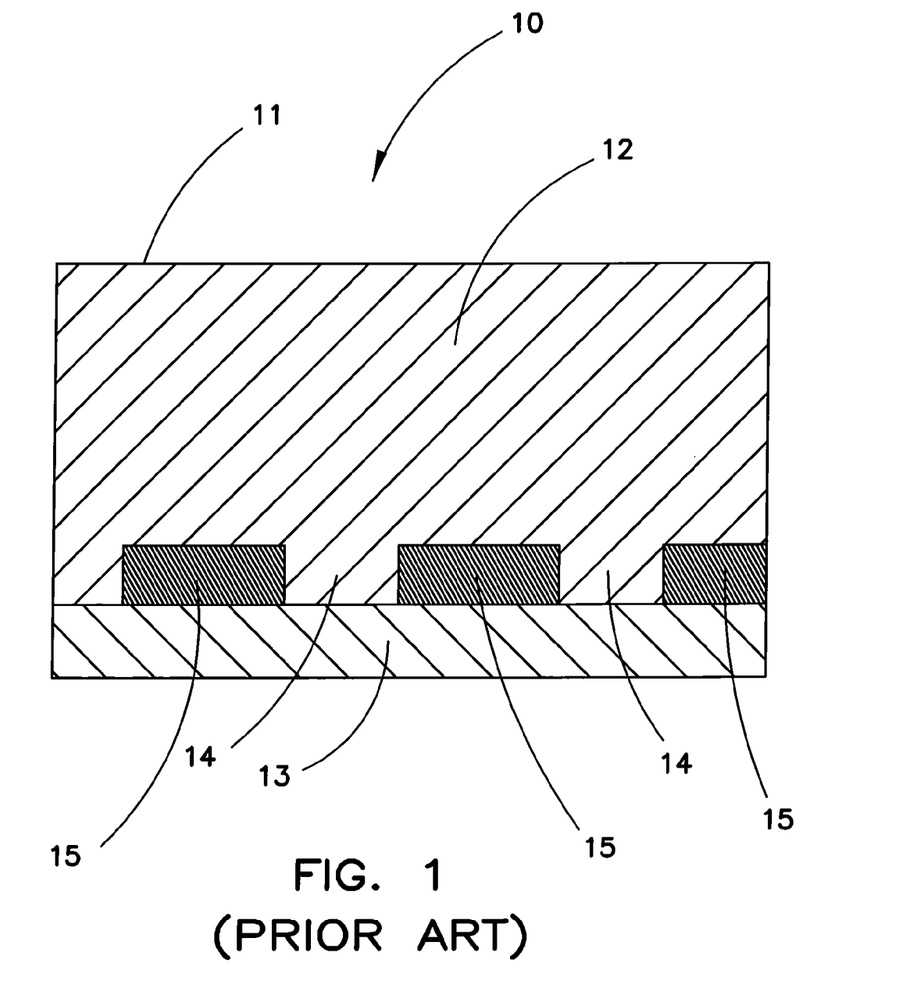
FIG. 1 is a partial longitudinal sectional view of a wall of a prior art tubular medical device.

Although the device of the '337 patent represents an improvement over prior art devices, it is desired to make still further improvements to such tubular devices to enhance their utility to an even greater degree than presently available. For example, FIG. 1 is a partial longitudinal sectional view of a wall 10 of a prior art tubular medical device 11 having outer and inner layers 12, 13 directly bonded to one another between spacings 14 of the windings of a coil 15 so that the two layers cannot axially move independently of each other. Because of a lack of independent movement, there can be a reduction in the overall bending flexibility of tubular medical device. Besides improving the bending flexibility of the tubular medical device, it would also be advantageous to further reduce kinkability in order for a physician to access more tortuous anatomy. Thus, it would be desirable to provide an arrangement of a coil in a tubular device that is highly resistant to kinking during use. It would also be desirable if the tubular device has a greater bending flexibility, i.e., a smaller bending radius, without kinking.

SUMMARY OF THE INVENTION

The foregoing problems are solved and a technical advance is achieved in a medical device comprising a sheath described herein, and a method of making of a sheath. In particular, various embodiments of a sheath are provided having the inner liner and the outer layer attachable to the coil independent from each other. This allows the inner liner and the outer layer the freedom to move coaxially independent from each other, which can provide greater bending flexibility.

The sheath preferably includes an inner liner, a coil, and an outer layer. The inner liner defines a lumen extending longitudinally through the sheath. The coil has a series of windings with an outer surface and inner surface. The windings are spaced from one another to define voids between adjacent windings. The coil is fitted around at least a part of the inner liner. An intermediate layer can be disposed between the inner surface of the coil windings and a portion of the inner liner. The intermediate layer is adapted to bond the inner surface of the coil to the inner liner. The outer layer is positioned over and attached to the outer surface of the coil, with the outer layer having a lower melt temperature than the inner liner.

The sheath can include a coil that is closely wound at a pre-determined coil spacing sufficient to inhibit portions of the outer layer from entering into voids between adjacent coil windings. Preferably, there is no outer layer material in the voids. The use of a coil, especially the relatively smaller coil spacing, can increase the kink resistance of the sheath.

The sheath can be constructed with a filler material disposed within the voids between the adjacent windings of the coil. The filler material has at least one dimension sized to bridge the void between adjacent coil windings in order to inhibit portions of the outer layer from bonding to the inner liner, which promotes the inner liner and the outer layer the freedom to move coaxially independent from each other. When the filler material is formed of a ribbon, it can have various cross-sectional shapes so long as the ribbon has a bridging dimension between adjacent windings, which can be along the outer surface, inner surface, and/or an intermediate surface therebetween. In one example, the ribbon can be shaped such that the intermediate region forms the bridging dimension, rather than the along the outer and inner surfaces, in order to form a pivot point for permitting the coil winding to pivot thereabout during bending of the medical device tube. In other examples, the filler material may be a resilient material or softer durometer material to allow the coil windings surrounding the filler material to move slightly longitudinally to compress or expand temporarily the filler material so that the bending flexibility is improved. Preferably, the outer layer has a lower melt temperature than the inner liner, the intermediate layer, and/or the filler material. At least one of the filler material, the outer layer, and the intermediate layer may also comprise of materials of a different durometer.

The sheath can include a second intermediate layer disposed between the outer surface of the coil windings and a portion of the outer layer and adapted to bond the outer surface of the coil to the outer layer. In one example, at least one coil winding can have only the intermediate layer, while at least one coil winding can have only the second intermediate layer. Preferably, the coil windings with this configuration can alternate. In another example, at least one coil winding can have both of the intermediate layer and the second intermediate layer, while at least one coil does not have either the intermediate layer or the second intermediate layer. Preferably, the coil winding with both layers can bound one or more coil windings without the layers.

In another embodiment, a method of making a sheath is also provided. The method can include one or more of the following steps: providing an inner liner, a coil having a series of windings with an outer surface and inner surface, an intermediate layer adapted to bond to the inner surface of the coil and to the inner liner, and an outer layer having a lower melt temperature than the inner liner; positioning the inner liner around a mandrel such that a lumen for said sheath is defined; fitting the coil around at least a part of the inner liner; disposing the intermediate layer between the inner liner and the coil; setting the intermediate layer in order to bond the inner surface of the coil to the inner liner; applying the outer layer around a portion of the coil to define an assembly; applying heat to the assembly such that the outer layer melts in order to adhere to the outer surface of the coil, wherein the inner liner and the outer layer are adhered to the coil independent from one another so that in response to bending said sheath the inner liner and the outer layer are capable of moving coaxially independent relative to one another.

Exemplary devices which can incorporate the disclosed sheath construction include, but are not limited to, balloon catheters (particularly, single lumen balloon catheters); stent deployment catheters, diagnostic, infusion and drainage catheters; endoscopes, laparoscopes and arthroscopes; guide catheters; and introducer sheaths.

Further objects, features, and advantages will become readily apparent to those skilled in the art after a review of the following detailed description of the preferred embodiments, with reference to the accompanying figures.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the axial ends of the tubular medical device, as well as the axial ends of various component features. The "proximal" end is used in conventional manner to refer to the end of the tubular medical device (or component) that is closest to the operator during use of the assembly. The "distal" end is used in conventional manner to refer to the end of the tubular medical device (or component) that is initially inserted into the patient, or that is closest to the patient.

Figure 2:
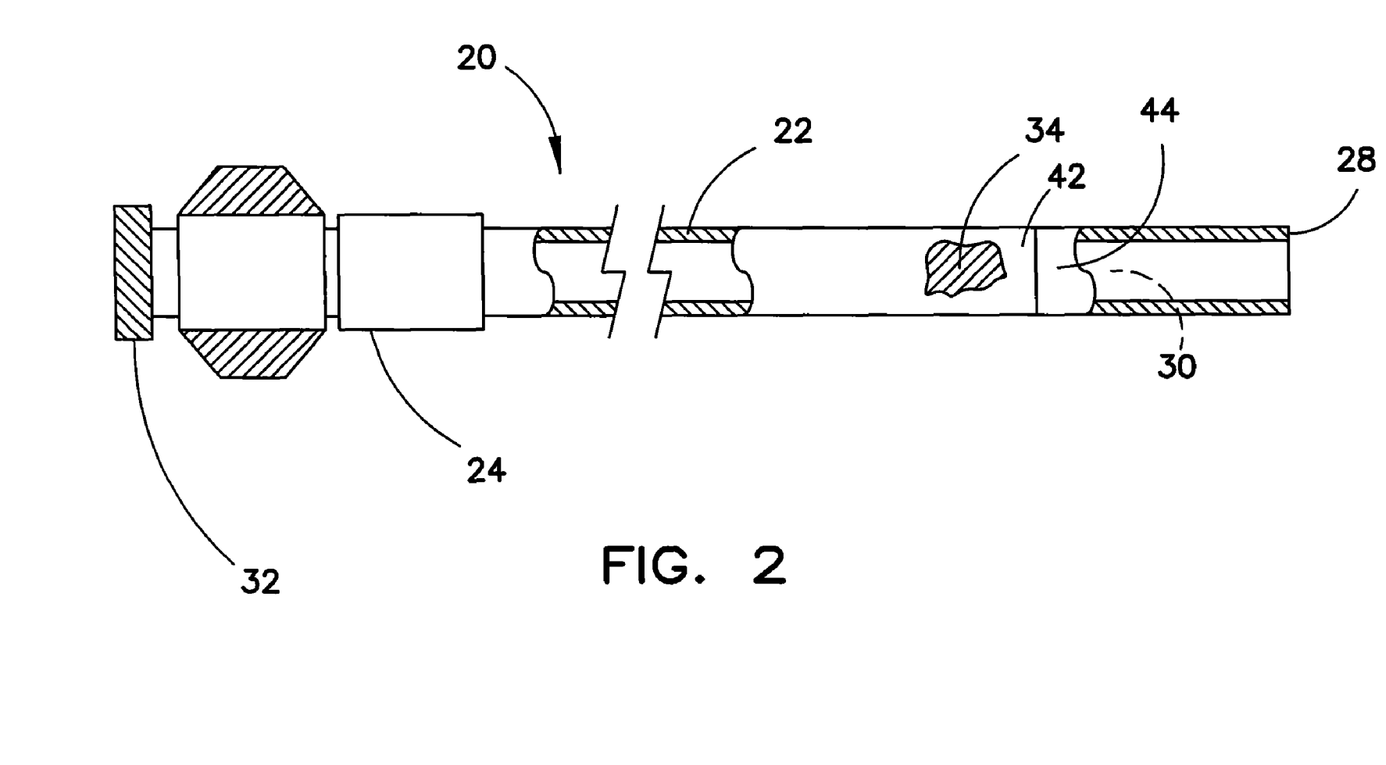
FIG. 2 is a partially cross-sectional view of one embodiment of a sheath.
Figure 3:
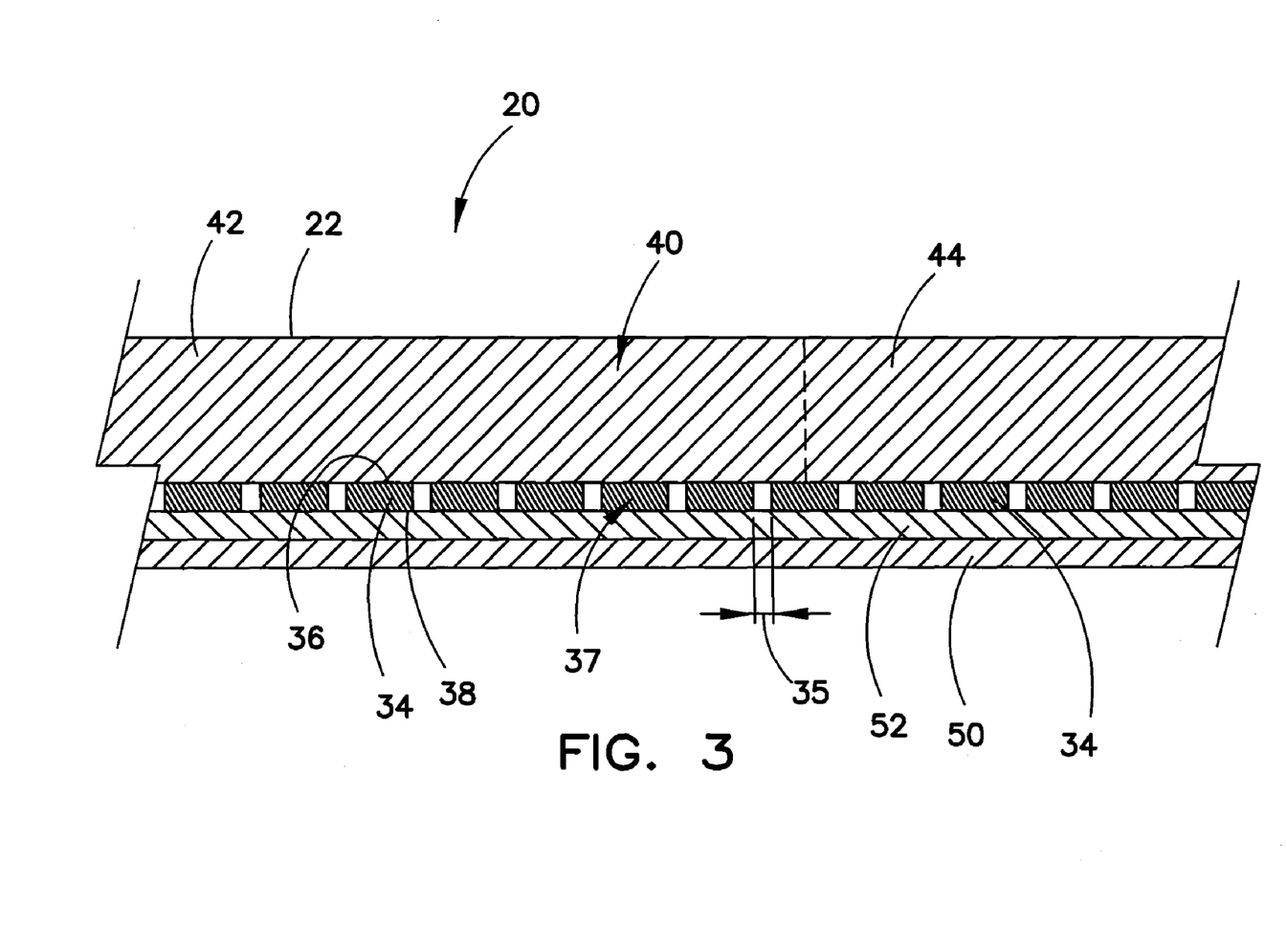
FIG. 3 is a partial cross-sectional view of a wall of the sheath illustrated in FIG. 2.

FIGS. 2 and 3 illustrate one embodiment of a sheath 20 that may be useful for performing any of a variety of minimally invasive medical procedures, including, for example, angioplasty, diagnosis, chemotherapy, drainage, endoscopy, laparoscopy and arthroscopy. Sheath 20 includes a proximal end 24, a distal end 28, and a lumen 30 extending longitudinally therethrough. Sheath 20 can extend in the distal direction from a conventional connector cap 32. The wall 22 of sheath 20 includes various layers. For instance, sheath 20 can include a reinforcement layer, such as a coil 34, sandwiched in between an outer layer 40 and an inner liner 50. An optional intermediate layer 52 can be disposed between coil 34 and inner liner 50 as described in greater detail below. A sheath including a coil within its wall can have improved kink resistance, crossability and reduced capability of necking.

Coil 34 can be made of ribbon or wire comprising a medical grade material, such as stainless steel or PEEK or other suitable polymer or metal. The cross-section of coil 34 can be a variety of shapes including rectangular (FIG. 3) or rounded, such as oval or semi-oval, as described later. Additional reinforcement layers such as a braid (not shown) extending over at least part of the coil may be included in the sheath, as described in the previously incorporated U.S. Pat. No. 6,939, 337. The braid would preferably comprise a plurality of crossed wires of circular or flat cross-section of medical grade metal such as stainless steel, or medical grade polymer such as aramid fiber materials (e.g., KEVLAR). Other medical grade materials may also be useful for the coil and the braid.

Outer layer 40 can be a medical grade polymer that is positioned over and contacting at least the coil in order to adhere to an outer surface 36 of one or more windings of coil 34. More preferably, outer layer 40 comprises heat-shrinkable (heat fused) tubing, such as a polyether block amide, polyamide (nylon), PTFE, and/or polyurethane. Any particular portion of sheath 20 can be given a flexibility or springiness which is different from the flexibility or springiness of the remainder of the tube. There are several ways in which this difference can be achieved. One way would be to vary the thickness of outer layer 40 along the length of sheath 20; however, this may not be a particularly practical way to achieve the desired difference. Another way is to permit outer layer 40 to comprise at least two discrete longitudinal segments (such as proximal segment 42 and distal segment 44 of differing durometer, as shown in FIG. 3. Making the distal segment 44 of outer layer 40 from a softer material than that from which the proximal segment 42 is made can yield a sheath with a tip that is more flexible or springier than the balance of the sheath.

Inner liner 50 is disposed beneath and along a portion of an inner surface 38 of one or more windings of coil 34. Inner liner 50 is made of a medical grade polymer, and may have a melt temperature greater than the melt temperature of outer layer 40. Inner liner 50 preferably comprises a lubricious polymer, such as PTFE, although it is appreciated that other lubricous polymers as determined by those skilled in the art can be used. Inner liner 50 is sized to define lumen 30 being suitably sized depending on the application, e.g., the lumen can be intended for the delivery of a diagnostic or therapeutic fluid, or the removal of a fluid from the patient.

Figure 3A:
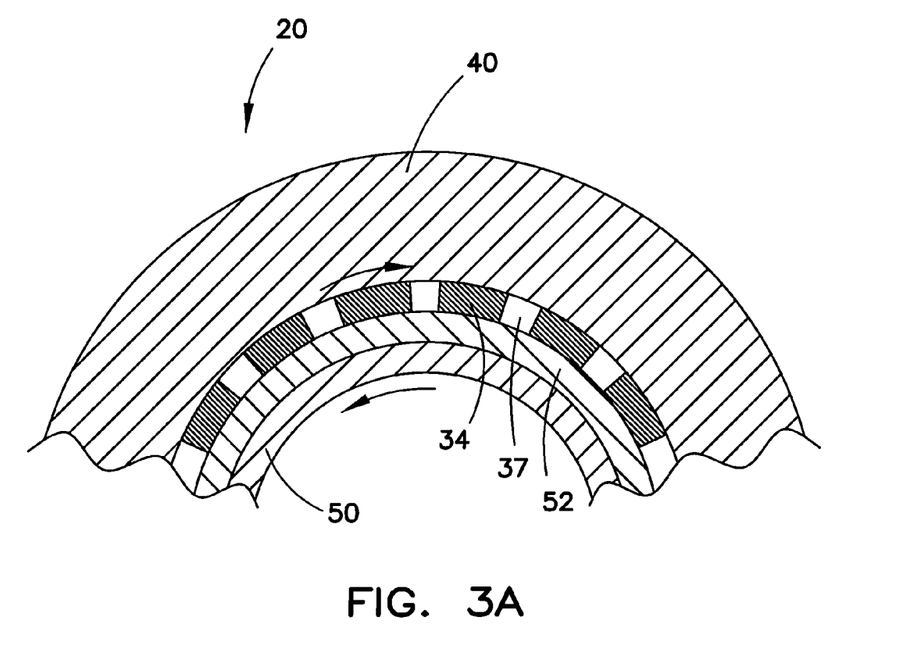
FIG. 3A is a partial cross-sectional view of a wall of the sheath illustrated in FIG. 3, depicting the sheath bent.

According to the embodiment of sheath 20 in FIG. 3, coil 34 is helically wound and spaced a distance 35 between its windings sufficient to substantially inhibit portions of outer layer 40 from entering into voids 37 defined between adjacent windings and from adhering to inner liner 50. To this end, coil 34 is preferably wound to have closely spaced windings so that the coil spacing 35 between adjacent windings can range from no spacing to between about 0.0005 inches up to 0.010 inches, although the coil spacing 35 can vary depending on the type of materials used for the inner liner and the outer layer and the desired kink resistance and bending flexibility from the coaxially independent movement from each of the inner liner and the outer layer. The use a filler material between adjacent windings as discussed below can be used with the closely spaced windings, or optionally can allow the coil spacing to be not as closely wound. FIG. 3A depicts sheath 20 being bent. By having inner liner 50 and outer layer 40 attached to coil 34 independent from each other can allow the inner liner and the outer layer the freedom to move coaxially independent from each other, represented by the arrows, which can provide greater bending flexibility than if attached to one another as is conventional. Independent movement from each of the layers may provide a slight torque to the coil winding cross-section.

Coil 34 permits the sheath to have a wall which is thinner than might conventionally be achieved, and to have more flexibility and springiness. During use, sheath 20 provides a sufficient stiffness for straightening in order to make it easier to control during advancement within the patient. Coil 34 also provides significant advantages during the manufacture of sheath 20, most notably, better control over the wall thickness ultimately possessed by the sheath.

To promote adhesion between the inner and outer surfaces of the coil and the respective inner liner and outer layer, outer surface 38 and inner surface 36 of coil 34, as well as the outer surface of inner liner 50, can be roughened in any conventional manner, such as by machine grinding or chemical etching, to form irregularities on the surface.

Intermediate layer 52 can be positioned along a portion of inner liner 50, beneath and in contact with at least part of the inner surface 38 of one or more coil windings. Intermediate layer 52 can provide a barrier to inhibit, if not eliminate, any direct adhesion between inner liner 50 and outer layer 40. Besides providing a barrier, intermediate layer 52 may also provide a bonding layer for adhering the inner surface 38 of coil 34 to the outer surface of inner liner 50. Although it is preferred that the intermediate layer comprises a single material for providing both barrier and bonding features, one skilled in the art would appreciate that the intermediate layer can comprise more than one material for providing the barrier feature and more than one material for providing the adhesive feature.

One embodiment of intermediate layer 52 comprises an adhesive material having a higher melt temperature than the material of outer layer 40. Any number of adhesives may be useful, including thermoplastic adhesives, thermoset adhesives, pressure sensitive adhesives, heat activated adhesives, chemically activated adhesives, and UV-curable adhesives, depending upon the application and desired results. The adhesives can be provided in liquid, solid or paste form. Adhesive materials may include, for example, polyamides, polyacrylamides, polyesters, polyolefins (e.g., polyethylene), polyurethanes, and the like. One preferred adhesive material for intermediate layer 52 includes a cyanoacrylate (e.g., Loctite 401, Rocky Hill, Conn.) or an ultraviolet adhesive (e.g., Loctite 3311).

Figure 4A:
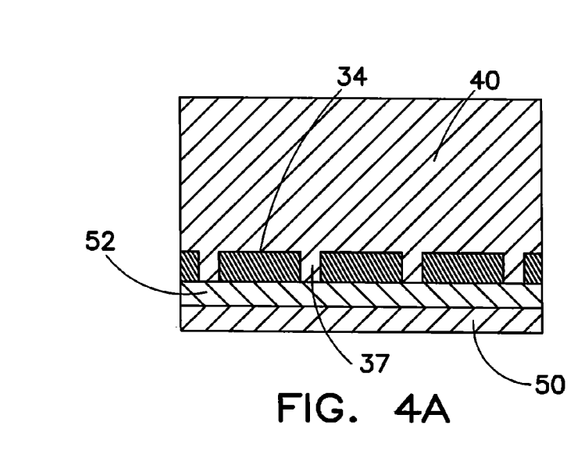
FIGS. 4A-4F are partial cross-sectional views of a wall of another embodiment of a sheath.

According to FIG. 3, intermediate layer 52 in combination with the predetermined coil spacing 35 of coil 34 can further inhibit the outer layer from attaching to the inner liner, even though in some sheath embodiments only the coil spacing (i.e., without the intermediate layer) provides this feature. In addition, FIG. 4A depicts another sheath embodiment that shows an instance where portions of the outer layer 40 fill the voids 37, but the intermediate layer 52 still inhibits the outer layer from attaching to the inner liner and thus the outer layer and inner liner are still capable of coaxial movement independent of each other.

According to FIGS. 4B-4F, the sheath 20 of any of the embodiments described herein may also include a filler material 60 disposed within the voids 37 between adjacent windings of coil 34 to provide a further barrier between outer layer 40 and inner liner 50. It is preferred that filler material 60 has a higher melt temperature than the material of outer layer 40. The filler material can comprise the same material as the intermediate layer or the inner liner, e.g., PTFE. The use of the filler material 60 allows the inner liner and the outer layer the freedom to move coaxially independent from each other, which can provide greater bending flexibility.

Besides having a higher melt temperature than the material of the outer layer, filler material 60 may also be soft material (i.e., lower durometer) and/or a resilient material so that the adjacent coil windings can longitudinally compress or expand the filler material during bending of the tube to permit additional movement of the coil windings for better bending flexibility. Filler material 60 can include a material having a durometer of about 30 to 60 on the Shore D hardness scale. Such materials, e.g., a nylon elastomer, more preferably have a durometer of about 35 to 50 on the Shore D hardness scale, and most preferably about 40. Even lower durometer materials may be preferred having a durometer of about 30-90 on the Shore A hardness scale. These lower durometer materials can include elastomers, rubbers, polyurethanes, as well as other materials as can be appreciated by those skilled in the art.

It may be desirable to apply different durometer filler materials along the sheath. For example, the distal portion of the sheath (e.g., up to about 5-10 cm) may include a durometer material of about 30-90 on the Shore A hardness scale. This can provide more resiliency between coil windings along this region, thereby allowing the coil windings to compress and expand the filler material. The inner liner and the outer layer are then given the freedom to move coaxially independent from each other, which can provide greater bending flexibility. Portions of the rest of the sheath, proximal to the distal portion, can include a durometer material of about 30 to 60 on the Shore D hardness scale. This can provide some flexibility to the sheath while also providing strength for pushability.

Figure 4B:
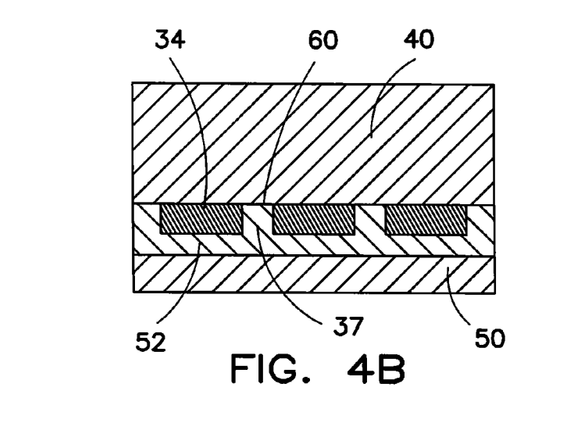

In the embodiment shown in FIG. 4B, intermediate layer 52 at least partially, if not completely, fills voids 37 to form the filler material 60, albeit the filler material can be a separate material from the intermediate layer. In one example, coil 34 can be pressed into the intermediate layer 52 in order to cause portions of the material of the intermediate layer to at least partially fill the voids 37. When the material of the intermediate layer overflows from the voids 37, the excess may be carefully removed so as not to provide an amount on the outer surface of the coil that would prevent adhesion between the outer layer and the outer surface of the coil. The intermediate layer 52 that can form the filler material can be a low durometer material such as described above.

In other embodiments, filler material 60 can be composed of a ribbon 62 that is located within voids 37, as shown in FIGS. 4C-4F. The cross-section of ribbon 62 has an outer surface 63 and an inner surface 64. Preferably, the filler material has at least one dimension 67 that bridges void 37 between adjacent windings laterally. In one example, the outer surface 63 of the ribbon 62 can have the dimension 67 in order to bridge the void 37 along the radially outward portion of the void adjacent outer layer 40. This dimensional feature can facilitate the inhibition of the material of the outer layer from entering into the void. The use of the ribbon can promote the independent coaxial independent of the inner liner and the outer layer. The ribbon 62 may also have a dimension 69 that extends in the radial direction, which provides greater structural integrity to the wall. The outer and inner surfaces 63, 64 of all of the embodiments of the ribbon 62 may be roughed or etched for better attachment to the respective inner and outer layers.

Figure 4C:
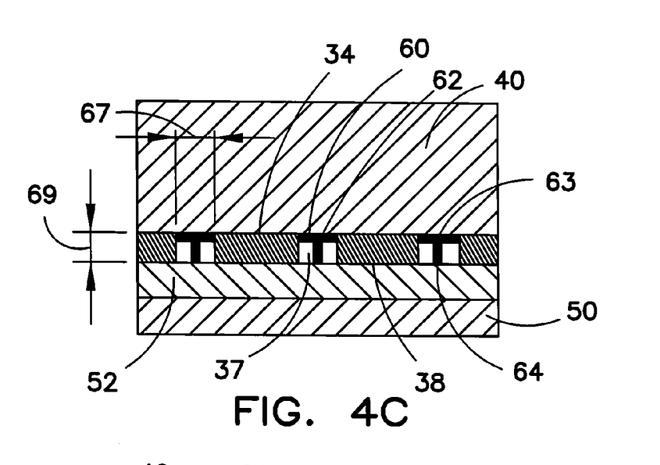
Figure 4D:
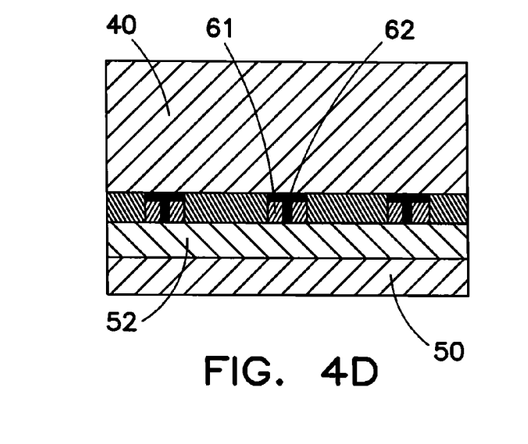
Figure 4E:
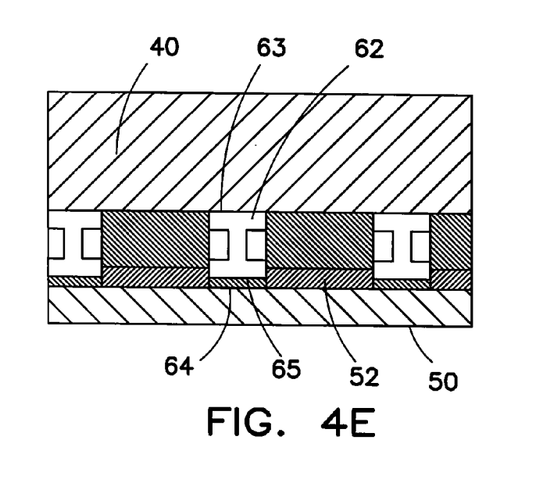
Figure 4F:
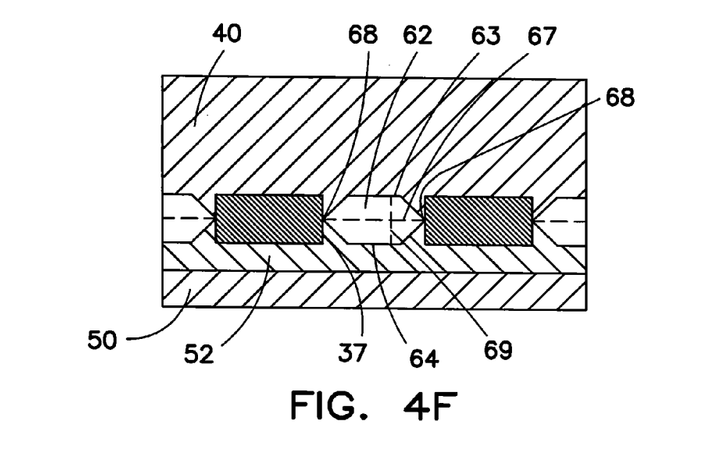

FIG. 4C depicts an instance where only the ribbon 62 fills the voids, which leaves areas immediately around the ribbon without any material to leave gaps. In FIG. 4D, ribbon 62 can be pressed into a second filler material 61. The second filler material 61 can be excess material from the intermediate material 52 as described herein, or can be a different material. In this arrangement, the second filler material 61 can aid in the orientation of the ribbon during construction and use. In FIG. 4E, the intermediate layer 52 is disposed only along the inner surface of the coil windings and the ribbon 62, shown as "I"-shaped, extends radially between the inner liner 50 and the outer layer 40, with areas around the ribbon without any material. An adhesive 65, such as the adhesives described herein, may be used along the inner surface 63 to ensure attachment between the ribbon 62 and the inner layer 50.

Figure 4G:
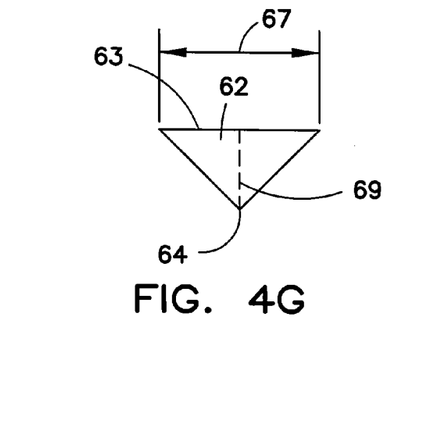
FIGS. 4G-4H are cross-sectional views of a filler material ribbon used with a sheath.

As can be seen from the figures, the cross-section of ribbon 62 can comprise a variety of shapes and sizes. For instance, the cross-section of ribbon 62 can be "T"-shaped, as shown in FIGS. 4C and 4D. The top portion of the T-shaped ribbon forms the outer surface 63 having the dimension 67 and the stem of the T-shaped ribbon has the dimension 69. One advantage of the T-shaped ribbon is that the stem is substantially smaller than the longitudinal spacing of void 37 and thus forms gaps around the stem that permits adjacent windings of coil 34 to have a certain degree of freedom to move longitudinally. Other shapes with dimension 67 along the outer surface 63, e.g., hexagonal (FIG. 4F), "I"-shaped (FIG. 4E), and triangular (FIG. 4G), as well as other shapes known in the art, such as rectangular and oval. It can be appreciated by one skilled in the art that the various shapes of the ribbon can be oriented upside down, e.g., "T"-shaped ribbon oriented upside down, so that the dimension 67 can extend across the bottom along the inner surface 64 of the ribbon 62.

Figure 4H:
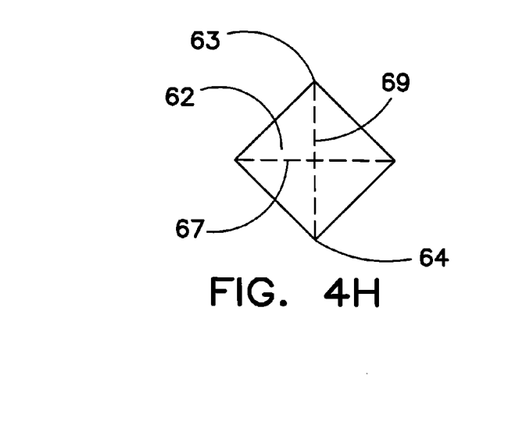

In some embodiments of the sheath, it is advantageous to extend dimension 67 across an intermediate area in between the inner and outer surfaces 64, 63 of ribbon 62. According to FIG. 4F (hexagonal) and FIG. 4H (diamond), the cross-section of ribbon 62 can be shaped to have a portion with dimension 67 extending across an intermediate area of the void 37, instead of along the top and/or bottom as in FIGS. 4C-4E. Because the portion with the dimension 67 is at the intermediate area, it can provide pivot points 68 for the coil winding so that bending flexibility is improved in all directions (e.g., 360 degrees). Thus, besides the inner and outer layers having independent coaxial movement, the coil winding can have an additional freedom of movement by pivoting about the pivot point 68 in the radial direction. The hexagonal cross-section also provides flattened surfaces along the outer and inner surfaces of ribbon 62 for better engagement with the respective outer layer, intermediate layer, and/or inner liner.

Figure 5A:
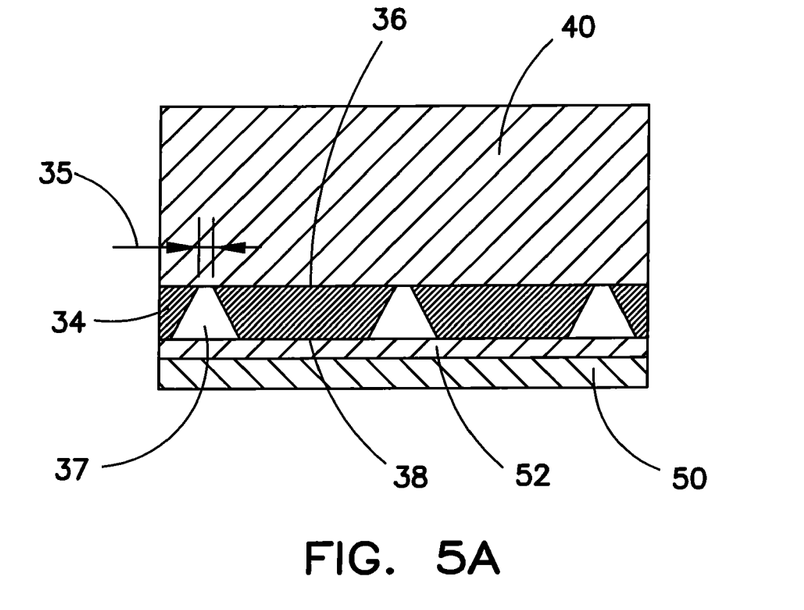
FIGS. 5A-5B are partial cross-sectional views of a wall of another embodiment of a sheath.
Figure 5B:
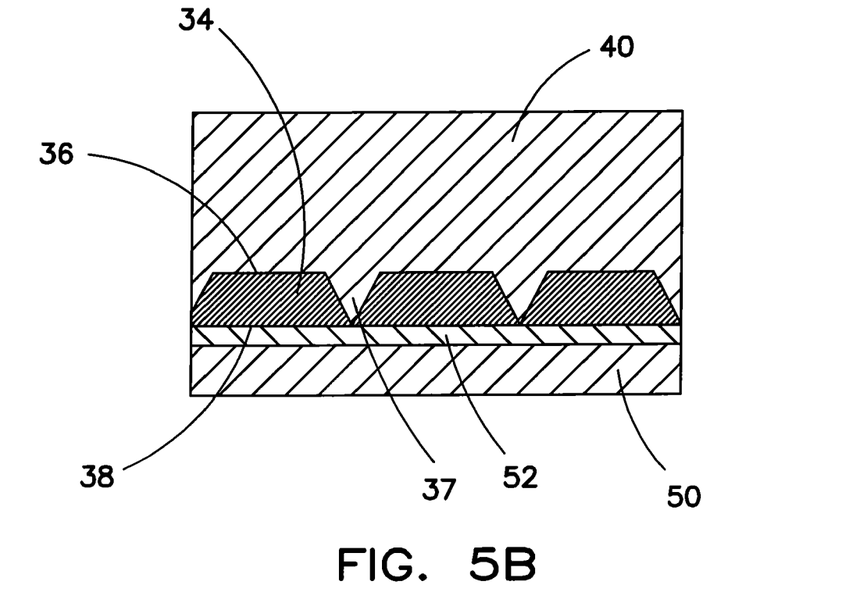

Although filler material 60 and ribbon 62 are shown in the figures be used with coils having a rectangular cross-section, it can be appreciated that they can be applied between adjacent coil windings having non-rectangular cross-sections. FIGS. 5A-5B depict the cross-section of the coil 34 as trapezoidal. For instance, in FIG. 5A the lengthier dimension of the trapezoidal cross-section is along the outer surface 36 of the coil 36 adjacent the outer layer 40, where the coil may be sized and oriented such that adjacent windings contact one another along the outer surface. The shorter dimension of the trapezoidal dimension is along the inner surface 38 so that the void 37 between adjacent windings is larger along the radially inner portion than along the radially outward portion of the void. According to FIG. 5B, the shorter dimension of the trapezoidal cross-section is along the outer surface 36 of the coil 34 adjacent the outer layer 40 so that the void 37 between adjacent windings is larger along the radially outward portion than along the radially inward portion of the void. The lengthier dimension of the trapezoidal dimension is along the inner surface 38, where the coil 34 may be sized and oriented such that adjacent windings contact one another along the inner surface. Narrowing the spacing between the lengthier sides of the trapezoidal cross-section of the coil can aid in the inhibition of the outer layer from bonding to the inner liner. Widening the spacing along the shorter sides of the trapezoidal cross-section of the coil can improve the freedom of movement between adjacent windings and improve the independent coaxial movement of the respective inner liner and the outer layer. It can be appreciated that the other structural features described herein can be applied in the embodiments in FIGS. 5A-5B.

Construction of sheath 20 of the illustrated embodiments will be now described. A mandrel is selected which has a diameter at least the size of the unstressed, free inner diameter of coil 34. Inner liner 50 can be placed on the mandrel in a known matter. When used, intermediate layer 52 can be sprayed, dipped, or otherwise applied over the outer surface of inner liner 50. Coil 34 can then be fitted or wrapped about the mandrel with inner liner 50 and/or intermediate layer 52, the mandrel temporarily maintaining coil 34 in an expanded condition with a diameter larger than the unstressed, free inner diameter. Coil 34 can be compression fitted or radially expanded attached during manufacture. Radially expanded fitting is described in the previously incorporated U.S. Pat.

No. 6,939,337. The outer surface of the coil, as well as the outer surface of the inner liner, may be roughened for improved adhesion.

Coil 34 can be wound by positioning a structure comprising the mandrel with the inner liner and/or the intermediate layer at the head and tail stock of a lathe. A coil transfer mechanism is mounted on the lathe carriage. The structure is rotated and the coil is wrapped thereon, as the coil transfer mechanism moves longitudinally parallel to the mandrel at the predetermined coil spacing 35. More details for applying a coil to form a tube can be found in U.S. Pat. No. 5,380,304 to Parker, which is incorporated by reference in its entirety. Optionally, the coil can be manually applied around the mandrel.

Finally, outer layer 40 can be established over coil 34, which is preferably formed from heat-shrinkable tubing. A heat reduced sleeve, e.g., FEP heat-shrinkable tubing (heat fused shrink tubing), may also be applied over the outer layer. The mandrel and the elements thereon are heated to shrink and cure outer layer 40 for heat setting thereof and to cause the outer layer to thermally bond to the outer surface 36 of coil 34 and/or intermediate layer 52 without bonding to inner liner 50. The inner surface 38 is bonded to the intermediate layer and/or the inner liner as shown in all of the figures. The mandrel and formed sheath 20 are then cooled, and the heat reduced sleeve is removed and the sheath is also removed from the mandrel.

Construction of sheath 20 of the described embodiments can have alternative steps to further inhibit the bonding between outer layer 40 and inner liner 50. For example, when intermediate layer 52 is a settable or curable material, an additional step of curing with an additional heat source the intermediate layer after application of coil 34 but before heat setting outer layer 40 (typically even before application of outer layer 40) can ensure bonding between the interior surface 38 of coil 34 to the outer surface of inner liner 50. As described herein, intermediate layer 52 may comprise a UV-curable adhesive and a UV light source is used to cure the intermediate later before the heating of the outer layer.

In other examples, intermediate layer 52 can be applied to inner liner 50 to a degree so that when coil 34 is fitted therearound, material of the intermediate layer at least partially fills, if not entirely fills, the voids 37 between adjacent windings to define the filler material 60, as shown in FIG. 4B. Excess material of the intermediate layer protruding outward from the void may then be wiped away, or otherwise eliminated, before application of the outer layer. Yet, in other examples, intermediate layer 52 can be applied to the inner surface of the coil while being transferred to the mandrel with inner liner 50 for winding.

In another example, during or after application of coil 34 to the mandrel with inner liner 50 and/or intermediate layer 52, filler material 60 can be separately applied within a substantial amount (50%-100%) of the voids 37 between adjacent windings of the coil. Filler material 60 can be applied by spraying, dipping, or introducing the filler material within the voids. When the filler material is ribbon 62, the ribbon can be applied during winding of coil 34 to the inner liner or even after the winding of the coil. As mentioned previously, the intermediate layer 52 can help fix the orientation of ribbon 62 by being pressed in into layer 52. When the intermediate layer is curable, a heat source can be applied to the intermediate layer for curing and setting the orientation of ribbon 62. It is appreciated that the above steps can be combined together or that even some steps may be eliminated as desired by those skilled in the art.

In one sheath embodiment, e.g., the sheath in FIG. 3, it may be desirable to allow the outer layer material to fill the voids, such as shown in FIG. 1, along the distal and proximal portions of the sheath (e.g., up to about 5-10 cm). The intermediate portion of the sheath, between the distal and proximal portions, can have one or more of the structural features described herein. This can strengthen the construction of the sheath at the ends, while allowing the coil windings along the intermediate portion some freedom move.

Figure 6A:
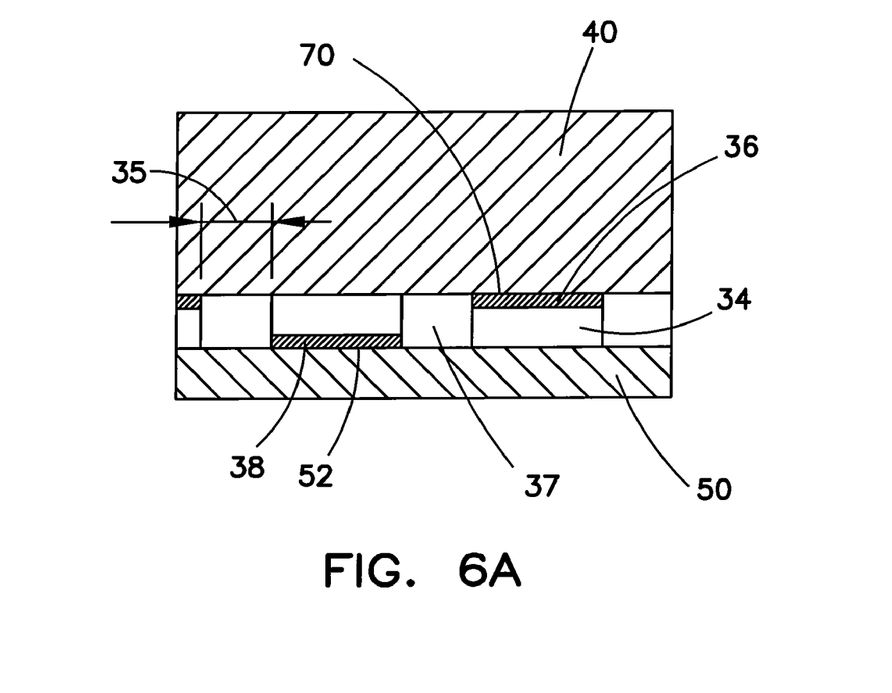
FIGS. 6A-6B are partial cross-sectional views of a wall of another embodiment of a sheath.
Figure 6B:
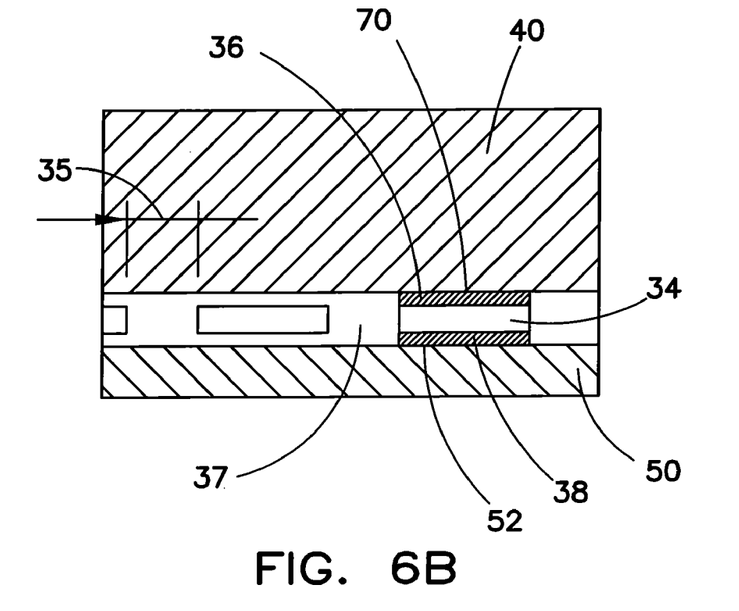

In another example, it may be desirable to apply a second intermediate layer 70, similar to the adhesive materials of the intermediate layer 52, along a portion of the outer surface 36 of coil 34, beneath the outer layer 40, as shown in FIG. 6A. The application of the intermediate layers can alternate with adjacent coil windings that are preferably closely spaced windings as described above. For example, the intermediate layer 52 can be applied to the inner surface of a coil winding, preferably every other coil winding, and the second intermediate layer 70 can be applied to outer surface of another coil winding, preferably every other coil winding that does not have the intermediate layer 52. As a result, the outer layer and inner liner are still capable of coaxial movement independent of each other. Alternatively, the application of the intermediate layers on the same coil winding, which is preferably closely spaced windings as described above, can alternate with every one, two, three, etc. coil windings, as shown in FIG. 6B. For example, the intermediate layer 52 can be applied to the inner surface of a coil winding, and the second intermediate layer 70 can be applied to outer surface of the same coil winding that has the intermediate layer 52. The adjacent coil winding does not have either intermediate layer attached thereto and thus is capable of moving between the inner liner and the outer layer. As a result, the outer layer and inner liner are still capable of coaxial movement independent of each other. It can be appreciated that the features in these figures can be applies to the other embodiments described herein.

The dimensions (for example, the thickness) of the various elements mentioned above should be selected in view of the purpose of medical device 20 in which sheath 20 is incorporated. It is believed that the selection of such dimensions will lie within the level of skill in the art of designing surgical instruments, once benefit of the present disclosure is had. While a modest amount of trial-and-error may be needed to obtain optimal dimensions, it is believed that any required experimentation will not be undue. The following may constitute the thicknesses of the various elements of a typical embodiment of sheath 20: inner liner 50, about 0.001-0.004 inches thick; coil 34, about 0.0015 to about 0.005 inches thick; and outer layer 40, about 0.0045-0.0065 inches thick.

The sheath 20 is particularly useful for the performance of a wide variety of catheterization procedures. The sheath 20 can be configured as a balloon catheter (particularly, a single lumen balloon catheter); a diagnostic, infusion or drainage catheter; an endoscope, laparoscope, arthroscope or the like; a guide catheter; or an introducer sheath, among other devices. The present invention is particularly advantageous over prior medical devices in that the sheath is resistant to collapse, necking and kinking during use and possesses improved bending flexibility during use. Moreover, the sheath 20 enjoys significant advantages during manufacture, having a highly uniform and repeatable inner and outer diameter.

The details of the construction or composition of the various elements of sheath 20 not otherwise disclosed are not believed to be critical to the achievement of the advantages of the present invention, so long as the elements possess the strength or mechanical properties needed for them to perform as disclosed. The selection of any such details of construction is believed to be well within the ability of one of even rudimentary skills in this area, in view of the present disclosure.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. A sheath for use with a medical device, comprising:
   an inner liner defining a lumen extending longitudinally through the sheath;
   a coil having a series of windings with an outer surface and inner surface, the coil having a predetermined coil spacing between adjacent coil windings to define voids between adjacent windings, the coil fitted around at least a part of the inner liner;
   an intermediate layer disposed between the inner surface of the coil windings and a portion of the inner liner and adapted to bond to the inner surface of the coil and to the inner liner; and
   an outer layer positioned over and attached to the outer surface of the coil, the outer layer having a lower melt temperature than the inner liner, wherein the inner liner and the outer layer are adhered to the coil independent from one another so that in response to the bending of said sheath the inner liner and the outer layer are capable of moving coaxially independent relative to one another.

2. The sheath according to claim 1, further comprising a filler material disposed within at least a portion of said voids between adjacent windings of the coil, the filler material having a dimension sized to bridge said void to inhibit portions of the outer layer from bonding to the inner liner, the filler material having a higher melt temperature than the outer layer.

3. The sheath according to claim 2, wherein portions of the intermediate layer at least partially fill the voids between adjacent coil windings to define the filler material.

4. The sheath according to claim 2, wherein the filler material comprises a first portion of a low durometer material disposed in a portion of voids between adjacent coil windings.

5. The sheath according to claim 4, wherein the filler material comprises a second portion of a material having a higher durometer than the first portion, disposed in a different portion of voids between adjacent coil windings than the first portion.

6. The sheath according to claim 2, wherein the filler material comprises a ribbon.

7. The sheath according to claim 6, wherein the ribbon has a cross-sectional shape having an outer surface and an inner surface, the outer surface of the ribbon disposed adjacent the outer layer proximate the outer surface of the coil and being dimensioned to bridge said void to inhibit portions of the outer layer from bonding to the inner liner.

8. The sheath according to claim 6, wherein the ribbon has a cross-sectional shape having an outer surface and an inner surface and an intermediate region therebetween, the intermediate region of the ribbon being disposed adjacent an intermediate portion of the coil and being dimensioned to bridge said void to inhibit portions of the outer layer from bonding to the inner liner.

9. The sheath according to claim 8, wherein the intermediate region of the ribbon contacts the intermediate portion of the coil winding to form a pivot point to permit the coil winding to pivot about said pivot point in response to bending of said sheath.

10. The sheath according to claim 6, wherein the ribbon has a cross-sectional shape having an outer surface and an inner surface, the inner surface of the ribbon disposed adjacent the inner liner proximate the inner surface of the coil and being dimensioned to bridge said void to inhibit portions of the outer layer from bonding to the inner liner.

11. The sheath according to claim 6, wherein at least a portion of the ribbon is surrounded by a second filler material.

12. The sheath according to claim 1, wherein the intermediate layer comprises a low durometer material.

13. The sheath according to claim 1, wherein the predetermined coil spacing is a distance sufficient to inhibit portions of the outer layer from entering into said voids between the adjacent coil windings.

14. The sheath according to claim 13, wherein the voids between adjacent coil windings include substantially no portion of the outer layer.

15. The sheath according to claim 1, further comprising a second intermediate layer disposed between the outer surface of the coil windings and a portion of the outer layer and adapted to bond the outer surface of the coil to the outer layer.

16. The sheath according to claim 15, wherein at least one coil winding has only the intermediate layer, and at least one coil winding has only the second intermediate layer.

17. The sheath according to claim 15, wherein at least one coil winding has both of the intermediate layer and the second intermediate layer, and at least one coil is without either the intermediate layer or the second intermediate layer.

18. The sheath according to claim 1, further comprising a distal portion and a proximal portion, each having a distance from the respective distal and proximal portions, wherein the inner liner and the outer layer are adhered to the coil independent from one another only along an intermediate portion of the sheath, defined between the distal and proximal portions.

19. The sheath according to claim 1, wherein the coil has a trapezoidal cross-section.

* * * * *